(12) United States Patent
Barker et al.

(10) Patent No.: US 11,759,155 B2
(45) Date of Patent: *Sep. 19, 2023

(54) METHODS AND SYSTEMS FOR COOLING OF AN IMAGING SYSTEM

(71) Applicant: GE Precision Healthcare LLC, Wauwatosa, WI (US)

(72) Inventors: David Barker, Salt Lake City, UT (US); Nathan Pack, South Jordan, UT (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/961,970

(22) Filed: Oct. 7, 2022

(65) Prior Publication Data

US 2023/0031790 A1 Feb. 2, 2023

Related U.S. Application Data

(63) Continuation of application No. 16/690,107, filed on Nov. 20, 2019, now Pat. No. 11,490,866.

(51) Int. Cl.
*A61B 6/00* (2006.01)

(52) U.S. Cl.
CPC .......... *A61B 6/4405* (2013.01); *A61B 6/4441* (2013.01); *A61B 6/4488* (2013.01)

(58) Field of Classification Search
CPC ... A61B 6/4488; A61B 6/4405; A61B 6/4441; A61B 6/032; A61B 6/037; A61B 6/447; A61B 6/035; A61B 6/4429; A61B 6/587; A61B 6/4458; A61B 6/4452; A61B 6/56; A61B 6/547; A61B 6/545; A61B 6/503; A61B 6/4482; G01N 23/203; G01N 2223/646; G01N 2223/3301; G01N 2223/631; G01N 2223/308; G01N 23/04; G01N 23/046; G21K 1/043; H01J 35/04; H01J 35/18; H01J 35/08; H01J 2235/1262; H01J 35/26; H01J 35/1024; H01J 35/106; H01J 35/13; H01J 35/16; H01J 35/153; H05G 1/04; H05G 1/025; H05G 1/02; H05G 1/10; H05G 1/12; F04D 29/605; F04D 29/588; H01R 35/04
USPC .................................. 378/122, 130, 198–200
See application file for complete search history.

(56) References Cited

U.S. PATENT DOCUMENTS

| | | | |
|---|---|---|---|
| 7,174,001 B2 * | 2/2007 | Andrews | H05G 1/025 378/141 |
| 10,820,871 B1 * | 11/2020 | Martinez Ferreira | A61B 6/4441 |
| 11,490,866 B2 * | 11/2022 | Barker | A61B 6/4488 |
| 2004/0196959 A1 * | 10/2004 | Weston | H05G 1/02 378/141 |

(Continued)

FOREIGN PATENT DOCUMENTS

DE 102013218285 A1 * 3/2015 ............ H05G 1/025

*Primary Examiner* — Irakli Kiknadze

(57) ABSTRACT

Various systems and devices are provided for an X-ray system. In one example, a mobile X-ray system, comprises a moveable arm comprising an X-ray source arranged at a first end and an X-ray detector arranged at a second end. The mobile X-ray system further comprises a cooling arrangement arranged within a housing shared with the X-ray source, wherein passages of the cooling arrangement do not extend outside the housing.

20 Claims, 5 Drawing Sheets

(56) References Cited

U.S. PATENT DOCUMENTS

| | | | | |
|---|---|---|---|---|
| 2005/0117706 A1* | 6/2005 | Powell | ................... | A61B 6/037 |
| | | | | 378/141 |
| 2008/0304625 A1* | 12/2008 | Dehler | ................. | A61B 6/4488 |
| | | | | 378/197 |
| 2015/0319831 A1* | 11/2015 | Fehre | ...................... | H05G 1/02 |
| | | | | 378/62 |

* cited by examiner

METHODS AND SYSTEMS FOR COOLING OF AN IMAGING SYSTEM

CROSS-REFERENCE TO RELATED APPLICATIONS

The present application is a continuation of U.S. patent application Ser. No. 16/690,107, filed Nov. 20, 2019, the disclosure of which is incorporated herein by reference in its entirety.

BACKGROUND

Embodiments of the subject matter disclosed herein relate to a heat exchanger arranged adjacent to an X-ray source of an X-ray system.

An X-ray imaging system comprises an X-ray source and an X-ray detector. X-rays emitted from the X-ray source can impinge on the X-ray detector and provide an X-ray image of an object or objects that are placed between the X-ray source and the detector. An imaging assembly may comprise a moveable support for adjusting an imaging angle and/or position. Additionally or alternatively, the X-ray source and the X-ray detector may be arranged on a main body of the X-ray imaging system, wherein the main body may be moveable relative to the moveable support.

During a scanning event, the X-ray source may demand cooling due to high amounts of current flowing therethrough. A cooling device, such as a heat exchanger, may be configured to flow coolant to the X-ray source.

BRIEF DESCRIPTION

In one embodiment, a mobile X-ray system, comprises a moveable arm comprising an X-ray source arranged at a first end and an X-ray detector arranged at a second end, and a cooling arrangement arranged within a housing shared with the X-ray source, wherein passages of the cooling arrangement do not extend outside the housing.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to embodiments of an X-ray system comprising a cooling arrangement. In one example, the cooling arrangement is arranged only in a moveable portion of the X-ray system. More specifically, the cooling arrangement is arranged directly adjacent to an X-ray source at a first end of an arm of the X-ray system. The cooling arrangement and the X-ray source may share a common housing (e.g., a casing). In one embodiment of the present disclosure, the common housing may partially seal the cooling arrangement and the X-ray source from atmosphere. In one example, the housing may seal only the X-ray source from atmosphere, while a portion of the housing containing the entirety of the cooling arrangement may comprise a vent or other opening. As such, outside of an opening to direct radiation to an X-ray detector of the X-ray system, the common housing and portion of the arm in which the X-ray source is arranged may be completely sealed.

A demand for the cooling arrangement may arise from continued developments in X-ray technology leading to increased current demands and smaller packaging sizes. Such developments may lead to increased cooling demands to accommodate increases in temperature while blocking thermal transfer from the X-ray source to neighboring components.

Previous examples of cooling arrangements included arranging a radiator of the cooling arrangement on a support of the arm, and routing cooling passages from the support through a support structure and into the portion of the arm where the X-ray source is located. However, such examples are inefficient, expensive to maintain and manufacture, and reduce a mobility of the X-ray system. Further examples include arranging the cooling arrangement in the arm, with cooling passages extending through an entire body of the arm. For example, this may include routing cooling passages from a first end of a C-arm to a second end, opposite the first end, of the C-arm. While mobility may be maintained in such examples, the cost of manufacture is still relatively high. Furthermore, a short-coming present in both previously described examples includes where the cooling arrangements are not configured to sufficiently cool the X-ray source independently. As such, a housing for the X-ray source in the previous examples comprises one or more openings for allowing the X-ray source to be at least partially cooled by atmospheric air. One issue with this approach is an increased packaging size as the X-ray source is arranged completely outside the main body of the arm to allow sufficient air flow to the X-ray source to achieve a desired cooling. Furthermore, cooling via ambient air may still be insufficient, increasing a likelihood of degradation. By doing this, the X-ray source is closer to the detector and a patient to be scanned, which may increase an X-ray dose received by the patient.

Figure 1:
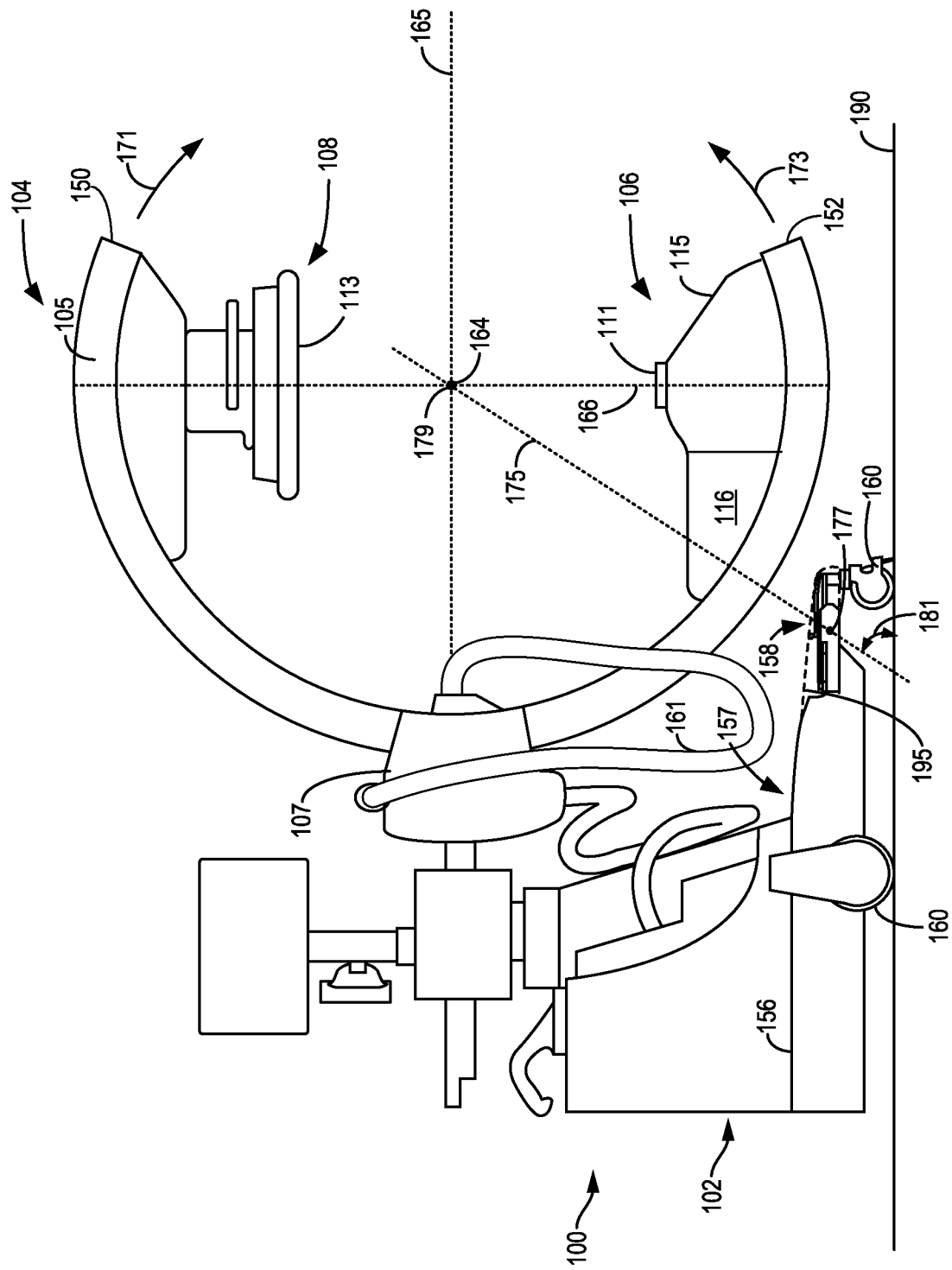
FIG. 1 is a side view of a medical imaging system including a C-arm, according to an embodiment.
Figure 2:
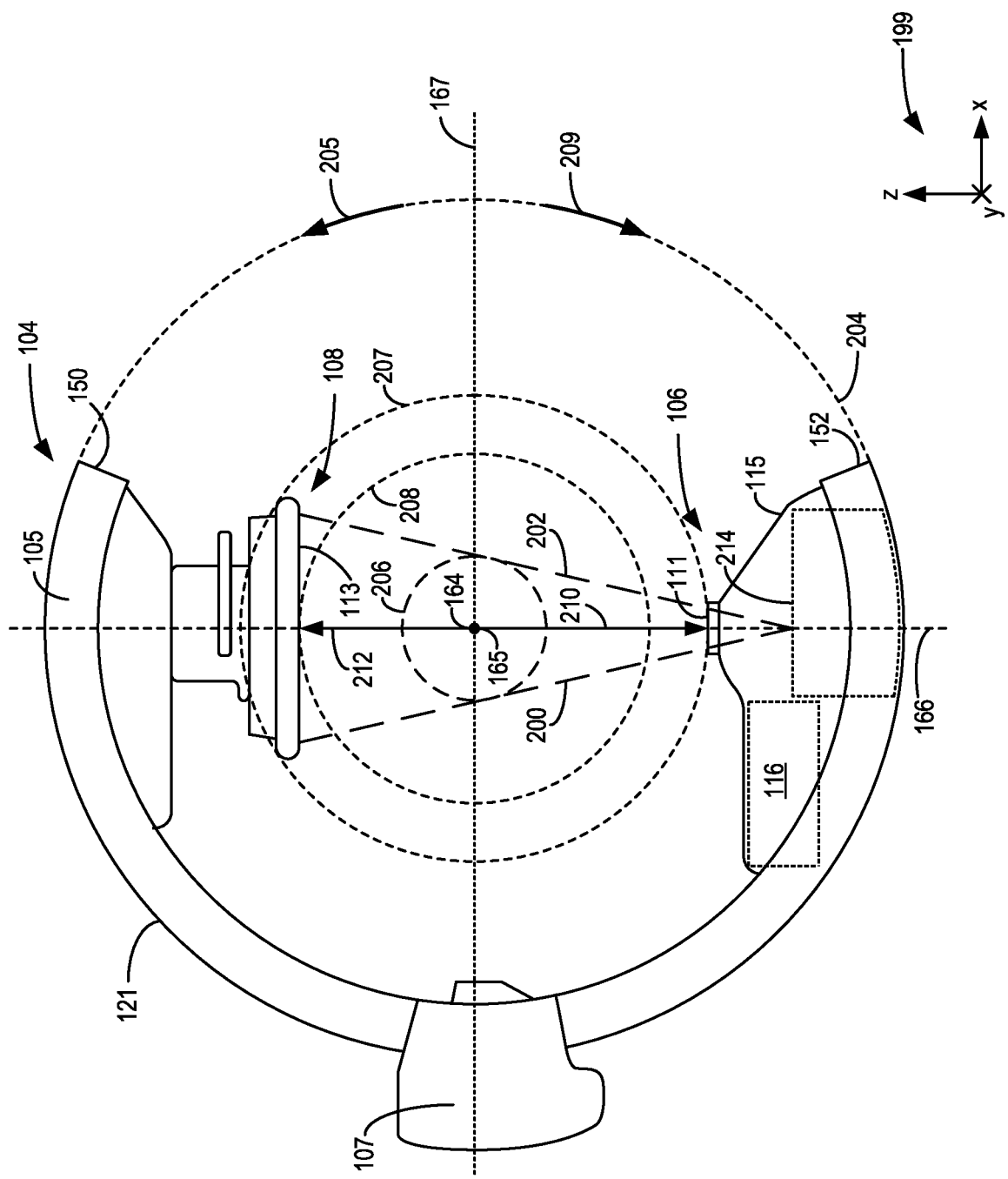
FIG. 2 is a partial view of the C-arm of FIG. 1 in a first position.
Figure 4:
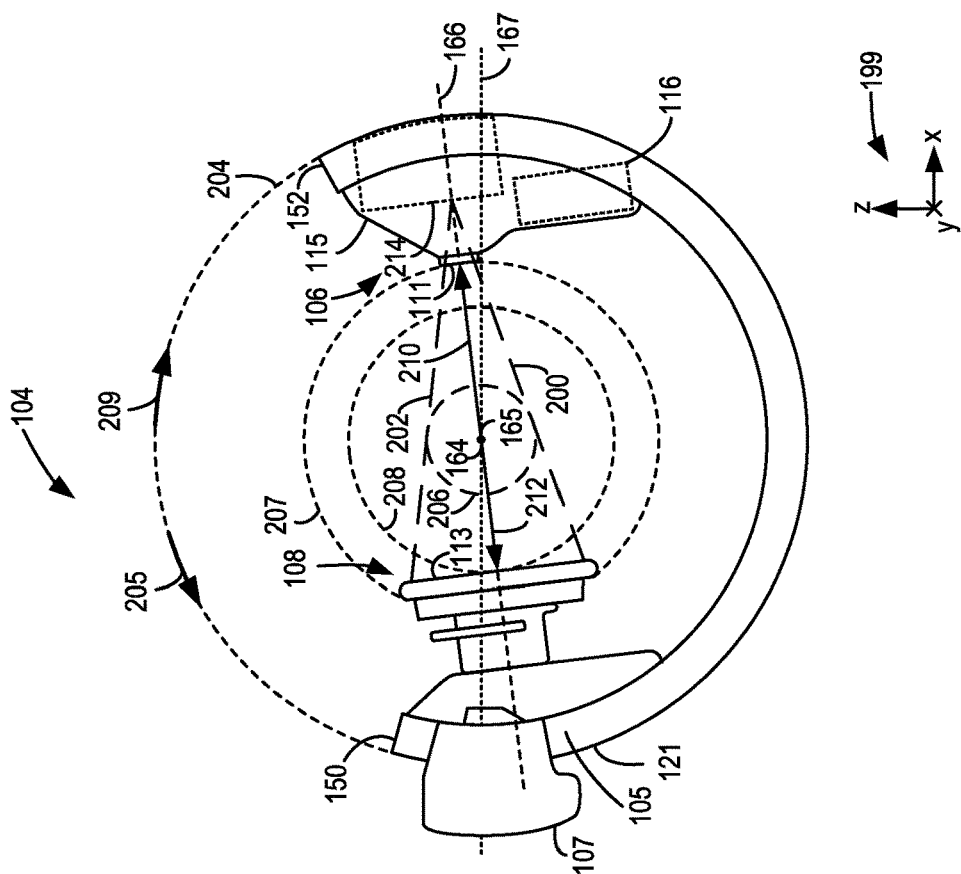
FIG. 4 is a partial view of the C-arm of FIGS. 1-3 in a third position.
Figure 3:
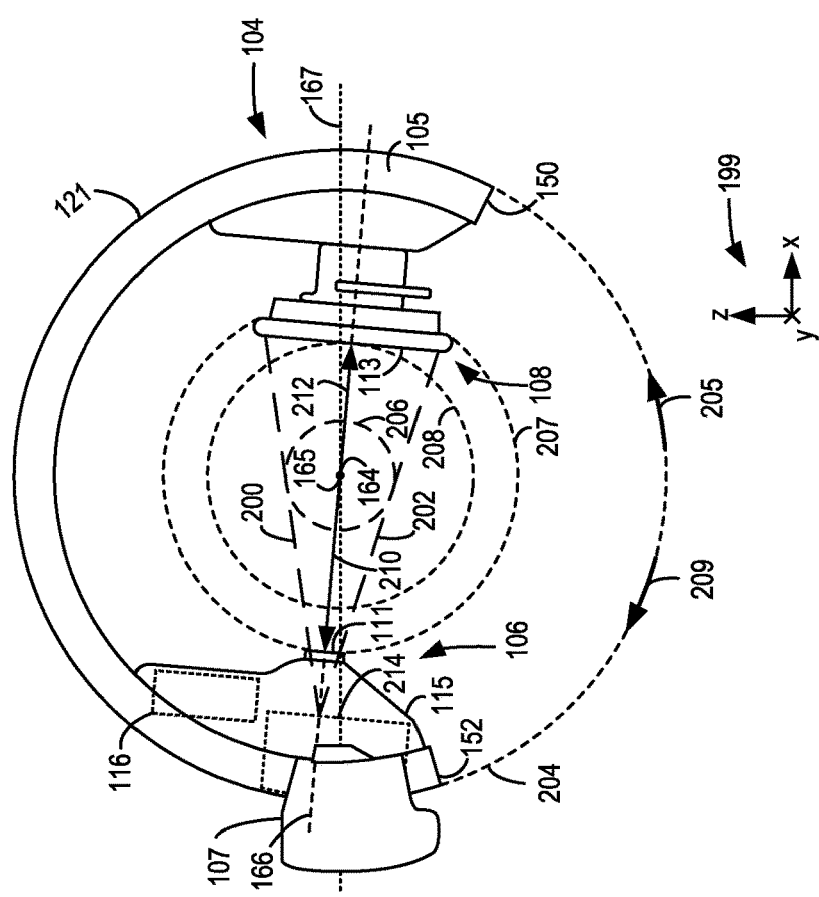
FIG. 3 is a partial view of the C-arm of FIGS. 1-2 in a second position.
Figure 5:
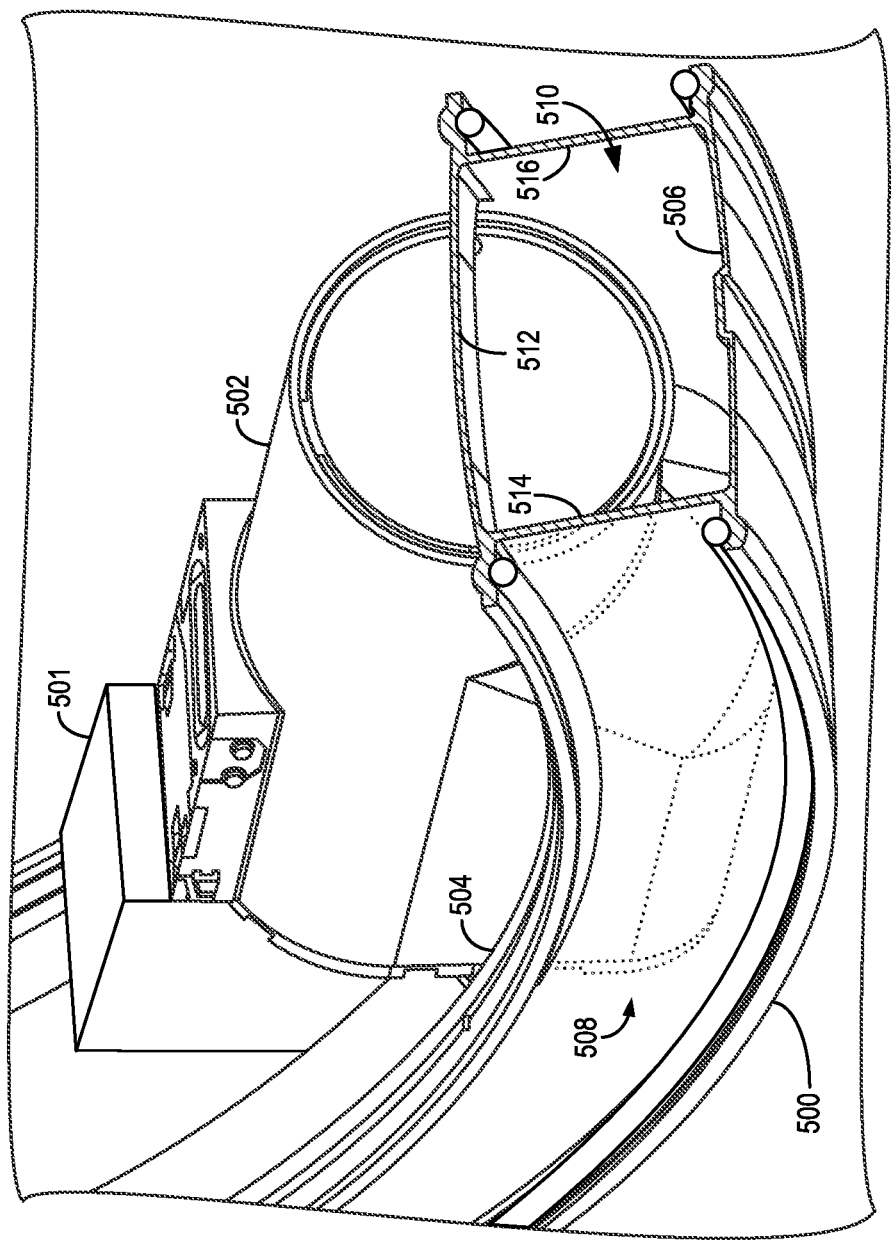
FIG. 5 is a perspective view of a portion of a C-arm housing a radiation source.
Figure 6:
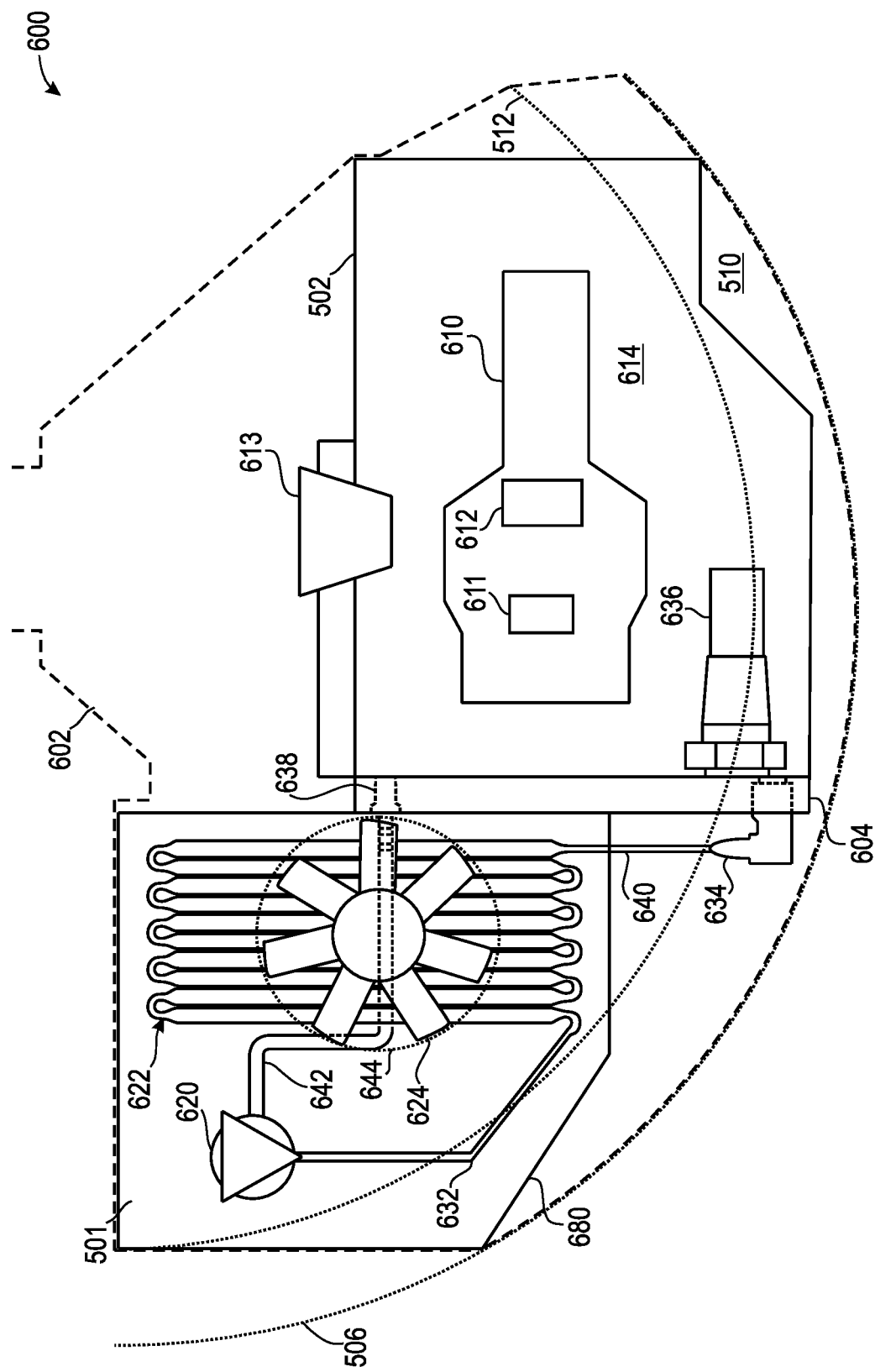
FIG. 6 shows a cross-sectional view of a cooling system and the radiation source arranged within a casing and a portion of a main body of the C-arm housing.

FIG. 1 illustrates a side view of a medical imaging system comprising the X-ray source and the cooling arrangement arranged at a first end of an arm. A detector may be arranged at a second end of the arm, wherein the second end is opposite the first end. FIGS. 2 through 4 illustrate a movement of the arm. As shown, the cooling arrangement and the X-ray source remain adjacent one another through the movement of the arm. FIG. 5 illustrates a perspective view of the X-ray source and the cooling arrangement. FIG. 5 further illustrates a submersion of a portion of the X-ray source into the main body of the arm such that portions of the X-ray source are housed by walls of the arm. FIG. 6 illustrates a cross-section of the first end of the arm, which exposes interiors of the arm, the X-ray source, and the cooling arrangement.

FIGS. 1 to 6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Turning to FIG. 1, a side view of an imaging system 100 is shown, where the imaging system includes C-arm 104 with a radiation source. In the examples described herein, the radiation source is an X-ray source 106 positioned opposite to X-ray detector 108. However, in other examples, the radiation source may be configured to emit a different type of radiation for imaging (e.g., imaging a patient), such as gamma rays, and the detector (e.g., X-ray detector 108) may be configured to detect the radiation emitted by the radiation source. The imaging system 100 additionally includes base unit 102 supporting imaging system 100 on ground surface 190 on which the imaging system 100 sits.

The C-arm 104 includes a C-shaped portion 105 connected to an extended portion 107, with the extended portion 107 rotatably coupled to the base unit 102. As an example, the C-arm 104 may be configured to rotate at least 180 degrees in opposing directions relative to the base unit 102. The C-arm 104 is rotatable about at least a rotational axis 164. The C-shaped portion 105 may be rotated as described above in order to adjust the X-ray source 106 and detector 108 (positioned on opposite ends of the C-shaped portion of the C-arm 104 along axis 166, where axis 166 intersects rotational axis 164 and extends radially relative to rotational axis 164) through a plurality of positions.

During an imaging operation, a portion of a patient's body placed in a clearance (e.g., gap) formed between the X-ray source 106 and detector 108, may be irradiated with radiation from the X-ray source. For example, X-ray source 106 may comprise an X-ray tube housed within casing 115, and X-ray radiation generated by the X-ray source 106 may emit from an outlet 111 of the casing 115 and may be intercepted by a detector surface 113 of the detector 108. The radiation may penetrate the portion of the patient's body being irradiated, and travel to the detector 108 where the radiation is captured. By penetrating the portion of the patient's body placed between the X-ray source 106 and detector 108, an image of the patient's body is captured and relayed to an electronic controller of the imaging system 100 (e.g., via an electrical connection line, such as electrically conductive cable 161).

The base unit 102 may include the electronic controller (e.g., a control and computing unit) that processes instructions or commands sent from the user input devices during operation of the imaging system 100. The base unit 102 may also include an internal power source (not shown) that provides electrical power to operate the imaging system 100. Alternatively, the base unit 102 may be connected to an external electrical power source to power the imaging system 100. A plurality of connection lines (e.g., electrical cables, such as electrically conductive cable 161) may be provided to transmit electrical power, instructions, and/or data between the X-ray source 106, detector 108, and the control and computing unit. The plurality of connection lines may transmit electrical power from the electrical power source (e.g., internal and/or external source) to the X-ray source 106 and detector 108.

The C-arm 104 may be adjusted to a plurality of different positions by rotation of the C-shaped portion 105 of the C-arm 104. For example, in an initial, first position shown by FIG. 1, the detector 108 may be positioned vertically above the X-ray source 106 relative to a ground surface 190 on which the imaging system 100 sits, with axis 166 arranged normal to the ground surface 190 intersecting a midpoint of each of the outlet 111 of X-ray source 106 and detector surface 113 of detector 108. The C-arm 104 may be adjusted from the first position to a different, second position by rotating the C-shaped portion 105. In one example, the second position may be a position in which the X-ray source 106 and detector 108 are rotated 180 degrees together relative to the first position, such that the X-ray source 106 is positioned vertically above the detector 108, with axis 166 intersecting the midpoint of the outlet 111 of the X-ray source 106 and the midpoint of the detector surface 113 of the detector 108. When adjusted to the second position, the X-ray source 106 may be positioned vertically above the rotational axis 164 of the C-shaped portion 105 of the C-arm 104, and the detector 108 may be positioned vertically below the rotational axis 164. Different example positions of the C-arm 104 rotated via the coupling between the extended portion 107 and C-shaped portion 105 are shown by FIGS. 2-4 and described further below.

As described above, the imaging system 100 includes X-ray source 106 positioned across rotational axis 164 relative to the detector 108. In the example shown by FIG. 1, detector 108 is positioned at a first end 150 of the C-shaped portion, and X-ray source 106 is positioned at an opposing, second end 152 of the X-ray source 106. In some examples, similar to those described further below, the C-shaped portion 105 includes an opening shaped to receive a casing of the X-ray source 106. The X-ray source 106 may comprise an X-ray tube (e.g., a vacuum tube configured to produce X-ray radiation) housed within the casing, and the X-ray tube may be seated within a clearance formed between opposing walls of the C-shaped portion 105 through the opening.

By arranging the X-ray tube to be positioned within the clearance of the C-shaped portion 105, a height of the X-ray source 106 (e.g., a length of the X-ray source 106 along axis 166 from the outlet 111 of the X-ray source 106 to the detector surface 113 of detector 108) may be reduced. The reduced height of the X-ray source 106 may increase an amount of open space between the detector surface 113 and the outlet 111 of the X-ray source 106, which may enable the C-arm 104 to accommodate larger patients for imaging and/or increase an ease of use of the C-arm 104 (e.g., increase an operating clearance of the C-arm 104) while maintaining the rotational axis 164 at the centered position between the first end 150 and the second end 152 (e.g., maintaining the rotational axis 164 an equal distance from each of the first end 150 and the second end 152 in the direction of axis 166). Maintaining the rotational axis 164 at the centered position may reduce a load (e.g., torque) on the C-shaped portion 105 during conditions in which the C-shaped portion 105 is rotated around the rotational axis 164 by reducing an eccentric motion of the C-shaped portion 105 relative to C-arms that do not include the rotational axis 164 at the centered position. As a result, a durability of the C-arm 104 may be increased and a likelihood of degradation of the C-arm 104 may be reduced.

In some examples, the C-shaped portion 105 of the C-arm 104 may be formed from a composite material, such as carbon fiber fabric. In one example, as described further below, the C-shaped portion 105 includes a plurality of grooved flanges, with each grooved flange formed from the composite material. In examples in which the composite material is carbon fiber fabric, the grooved flanges may be formed through layering of a plurality of layers of the carbon fiber fabric, with one or more layers having a different carbon fiber orientation relative to other layers. Due to a strength of the carbon fiber fabric (e.g., a rigidity and/or load potential), the grooved flanges may maintain the C-shaped portion 105 of the C-arm 104 in engagement with the extended portion 107 while also decreasing the weight of the C-shaped portion 105 relative to C-arms that do not include grooved flanges formed from the composite material. Further, in some examples, the weight of the C-shaped portion 105 may be further reduced by forming one or more walls of the C-shaped portion 105 from the composite material. By forming the grooved flanges and/or walls of the C-shaped portion 105 from the composite material, the weight of the C-shaped portion 105 may be reduced and a load on the imaging system may be decreased (e.g., a load on a motor of the imaging system configured to rotate the C-shaped portion 105 around the rotational axis 164).

A cooling arrangement 116 may also be housed within the housing 115 and the second end 152 of the main body 105. Dashed line illustrates an imaginary division between the cooling arrangement 116 and the X-ray tube within the housing 115. An entirety of the cooling arrangement 116 is arranged at the second end 152 such that no portion of the cooling arrangement 116 extends beyond a profile of the housing 115. In one example, the housing 115 is a single continuous piece. Additionally or alternatively, outside of the outlet 111, the housing 115 may be completely sealed such that gases and liquids may not enter the housing 115. In one example, additionally or alternatively, the housing 115 is a continuation of the main body 105 such that the housing and second end 152 of the main body 105 are physically coupled to one another. The cooling arrangement and the X-ray tube within the housing 115 and the main body 105 are described in greater detail below.

Referring collectively to FIGS. 2-4, various example positions of the C-shaped portion 105 are shown. Specifically, FIG. 2 shows the C-shaped portion 105 in a first position in which the axis 166 between the detector surface 113 and the outlet 111 of the X-ray source 106 is arranged perpendicular to the ground surface 190 on which the imaging system 100 sits (shown by FIG. 1, with axis 167 being an axis parallel to the ground surface 190 and perpendicular to a direction of gravity and rotational axis 164). FIG. 3 shows the C-shaped portion 105 in a first rotated position in which the X-ray source 106 is positioned closer to extended portion 107 and detector 108 is positioned further from extended portion 107 relative to the first position shown by FIG. 2, and FIG. 4 shows the C-shaped portion 105 in a second rotation position in which the detector 108 is positioned closer to the extended portion 107 and the X-ray source 106 is positioned further from the extended portion 107 relative to the first position. Cable 161 shown by FIG. 1 is omitted from FIGS. 2-4 for illustrative clarity. A rotational range of the C-shaped portion 105 (e.g., an amount of angle through which the C-shaped portion 105 may rotate relative to the base unit 102) may be greater than 180 degrees. As one example, FIG. 3 may correspond to a rotation of the C-shaped portion 105 by an angle of 95 degrees around the rotational axis 164 relative to the position shown by FIG. 2, and FIG. 4 may correspond to a rotation of the C-arm 104 by an angle of −95 degrees around the rotational axis 164 relative to the position shown by FIG. 2, with the C-shaped portion 105 rotating through 190 degrees to adjust from the position shown by FIG. 4 to the position shown by FIG. 3. In each of FIGS. 2-4, the extended portion 107 is maintained in position (e.g., not rotated) relative to the C-shaped portion 105, with the position of extended portion 107 in FIGS. 2-4 being the same as the position of extended portion 107 shown in FIG. 1 (e.g., with the extended portion 107 not rotated relative to the ground surface 190 or axis 167).

Each of FIGS. 2-4 show axis 200 and axis 202 illustrating a radiation emission pathway of the X-ray source 106. Specifically, the X-ray source 106 may emit a beam of X-ray radiation between the axis 200 and axis 202, where axis 200 and axis 202 represent rays of the beam directed toward detector surface 113. As the C-shaped portion 105 rotates around the rotational axis 164 (e.g., for imaging of a patient or object to be imaged that is positioned at the rotational axis 164), the beam of X-ray radiation remains directed toward the detector surface 113 due to the concurrent rotation of each of the detector 108 and X-ray source 106 around the rotational axis 164. While rotating isocentrically around the rotational axis 164, the C-shaped portion 105 may move along rotation pathway 204 (e.g., in isocentric rotation direction 205 or opposing isocentric rotation direction 209), and because the X-ray source 106 and detector 108 rotate around the rotational axis 164 along with the C-shaped portion 105, the beam of X-ray radiation emitted by the X-ray source 106 forms an isocentric imaging area 206 of the imaging system 100 (shown by FIG. 1, the imaging system 100 including C-arm 104).

An isocenter 165 of the C-arm 104 is positioned at the rotational axis 164. Specifically, the isocenter 165 of the C-arm 104 is positioned at an intersection of rotational axis 164 and axis 167. Each of the first end 150 and second end 152 may be positioned a same length from the isocenter 165. For example, an outer surface 121 of the C-shaped portion 105 may have a uniform radius of curvature in a direction around the rotational axis 164 (e.g., a same radius of curvature at each location along the outer surface 121 in the direction around the rotational axis 164, with the isocenter 165 being the center of curvature) such that each portion of the outer surface 121, including portions positioned at the first end 150 and second end 152, is positioned a same distance from the isocenter 165 along axis 166 (e.g., as indicated by rotation pathway 204 having a same radius of curvature as the outer surface 121). As described above, the C-shaped portion 105 may rotate around the rotational axis 164 (e.g., via the coupling between the C-shaped portion 105 and the extended portion 107). In some examples, C-shaped portion 105 may also rotate around axis 167. In this configuration, the C-shaped portion 105 may rotate around either of rotational axis 164 or axis 167 (or both of rotational axis 164 and axis 167), where axis 167 is orthogonal to the rotational axis 164. In the views shown by FIGS. 2-4, however, the C-shaped portion 105 is rotated only around the rotational axis 164 and not the axis 167.

Although the first end 150 and second end 152 may be positioned the same length from the isocenter 165, each of detector surface 113 and outlet 111 may be positioned different lengths from the isocenter 165. For example, FIGS. 2-4 show a rotation pathway 207 of the outlet 111 and a rotation pathway 208 of the detector surface 113, with each of the rotation pathway 207 and rotation pathway 208 being of circular shape. Outlet 111 may move along rotation pathway 207 and detector surface 113 may move along rotation pathway 208 during conditions in which the C-shaped portion 105 is rotated around rotational axis 164. However, a length 212 (e.g., a diameter of the rotation pathway 208) from the isocenter 165 to the detector surface 113 may be smaller than a length 210 (e.g., a diameter of the rotation pathway 207) from the isocenter 165 to the outlet 111. As one example, the length 210 may be larger than the length 212 due to the X-ray source 106 being seated within a portion of the C-shaped portion 105. For example, X-ray tube 214 is shown schematically and illustrated by dashed lines in FIGS. 2-4 to indicate that the X-ray tube 214 is housed within casing 115 and seated within a portion of the C-shaped portion 105.

The seated position of the X-ray tube 214 within the C-shaped portion 105 may enable the outlet 111 to be positioned closer to the second end 152 compared to configurations in which the X-ray tube is not seated within the C-shaped portion, which may result in a decreased height of the X-ray source 106 (e.g., a decreased height of casing 115 of the X-ray tube 214). As described above, the resulting reduced height of the X-ray source 106 may increase the amount of open space between the detector surface 113 and outlet 111 (e.g., increase the length 210 between the isocenter 165 and the outlet 111 relative to the length 212 between the isocenter 165 and the detector surface 113), which may enable the C-arm 104 to accommodate larger patients and/or increase ease of use of the C-arm 104.

Further, in some examples, the seated position of the X-ray source 106 within the C-shaped portion 105 may increase a balance of the C-arm 104, which may reduce a likelihood of undesired vibration of the C-arm 104. For example, in some embodiments, the C-shaped portion 105 may be formed of a composite material, such as carbon fiber fabric. The carbon fiber fabric may provide increased strength to the C-shaped portion 105 and/or a reduced weight of the C-shaped portion 105 relative to C-arms that include a C-shaped portion formed of a different material (e.g., steel, aluminum, etc.). However, due to the reduced weight of the C-shaped portion 105 resulting from the composite material, balance characteristics of the C-shaped portion 105 may be different compared to C-shaped portions formed from other materials such as metal. By seating the X-ray source 106 within the C-shaped portion 105 formed of the composite material, the balance characteristics of the C-shaped portion 105 may be increased.

Further, in some examples, the seated position of the X-ray source 106 within the C-shaped portion 105 may increase the balance of the C-arm 104 during isocentric rotation (e.g., symmetric rotation around the isocenter 165, as described above). As one example, the seated position of the X-ray source 106 may provide counterweight to a weight of the detector 108, such that a load and/or vibration of a motor of the imaging system driving the rotation of the C-arm 104 is reduced compared to configurations that do not include the X-ray source 106 seated within the C-shaped portion 105.

Additionally or alternatively, as depicted in the various positions of the C-arm 104 in FIGS. 2-4, a position of cooling arrangement 116 relative to the X-ray tube 214 does not change. In this way, a distance coolant travels from the cooling arrangement 116 to the X-ray tube 214 remains constant independent of a position of the C-arm 104. Furthermore, by arranging the cooling arrangement 116 within the housing 115 with the X-ray tube 214, the cooling arrangement and the X-ray tube 214 may be easily serviced via removal of the housing 115.

Referring now to FIG. 5, a perspective view of a second end of a C-shaped portion 500 of a C-arm of an imaging system is shown. In one example, the second end of the C-shaped portion 500 may be the second end 152 of the C-shaped portion 105 described above with reference to FIGS. 1-4. The C-shaped portion 500 includes an opening 504 shaped to receive an X-ray tube 502 and a cooling arrangement 501, where the X-ray tube 502 is seated within the C-shaped portion 500 against an interior surface of an outer circumferential wall 506 (e.g., as illustrated by broken lines 508 indicating a position of the X-ray tube 502 within an interior clearance 510 of the C-shaped portion 500). In some examples, the X-ray tube 502 may be the X-ray tube 214 described above with reference to FIGS. 2-4. Additionally or alternatively, the cooling arrangement 501 may be the cooling arrangement 116 of FIGS. 1-4.

As illustrated, the cooling arrangement 501 may be spaced away from the outer circumferential wall 506 such that a bottom of the cooling arrangement 501 does not touch the outer circumferential wall 506. However, the cooling arrangement 501 may be arranged such that it is at least partially arranged within the interior clearance 510. The portions of the X-ray tube 502 and the cooling arrangement 501 arranged outside of the interior clearance 510 may be covered via a housing, such as housing 115 of FIG. 1.

The interior clearance 510 of the C-shaped portion 500 is a hollow portion of the C-shaped portion 500 formed by each of the outer circumferential wall 506, inner circumferential wall 512, first sidewall 514, and second sidewall 516. The opening 504 is formed through the inner circumferential wall 512 from an exterior surface 518 of the inner circumferential wall 512 to the interior clearance 510. In some examples, the interior clearance 510 may extend an entire length of the C-shaped portion 500 from a first end to a second end (e.g., similar to first end 150 and second end 152 described above), and the interior clearance 510 may be closed at both ends of the C-shaped portion 500. Additionally or alternatively, the interior clearance may extend only as far as a circumferential length of the opening 504. In one example, the opening 504 is sized and shaped to receive only the housing of the cooling arrangement 501 and the X-ray tube 502. In some examples, an entirety of the X-ray tube 502 may be positioned within the interior clearance 510. In other examples, a different amount of the X-ray tube 502 (e.g., at least half of the X-ray tube 502) may be positioned within the interior clearance 510.

Turning now to FIG. 6, it shows a cross-section 600 of the X-ray tube 502 and the cooling arrangement 501. The cross-section 600 further includes housing 602, which may be a non-limiting example of housing 115 of FIG. 1. The housing 602 may be a single, continuous piece configured to separate shield each of the X-ray tube 502 and the cooling arrangement 501.

As illustrated, the housing 602, illustrated in larger dashes, may house an entirety of the X-ray tube 502 and the cooling arrangement 501. As such, no components of the cooling arrangement 501 and the X-ray tube 502 may extend beyond a profile of the housing 602. The housing 602 may be further shaped to contain bottom portions of the X-ray tube and the cooling arrangement 501 such that the housing 602 is at least partially positioned within the clearance 510 and in face-sharing contact with the outer circumferential wall 506, illustrated via smaller dashes. Larger dashes are larger than smaller dashes. As such, if service of the X-ray tube and/or cooling arrangement 501 is desired, the entire housing 602 may be removed from the first end of the C-arm, resulting in the removal of both the cooling arrangement 501 and the X-ray tube 502.

The cooling arrangement 501 may be coupled to the X-ray tube 502 via an interface 604. As shown, the interface 604 may be physically coupled to each of the cooling arrangement 501 and the X-ray tube 502. The interface 604 comprises a plurality of ports fluidly coupling the cooling arrangement 501 to an interior volume 614 of the X-ray tube 502. In one example, a X-ray insert 610 comprising a cathode 611 and an anode 612 may be arranged in the X-ray tube 502. The cathode 611 may be configured to receive current from a connector, which may excite electrons on the cathode 611 and cause them to flow toward the anode 612. This may result in radiation which may exit the housing 610 toward an outlet 613, and to a detector. In one example, the interface 604 may be further shaped to receive one or more conductors of the connector to flow current to the cathode 611. Additionally or alternatively, the interface 604 may be one example of a high-voltage connector, comprising conductive pins for physically coupling the interface 604 to the X-ray tube 502. Additionally or alternatively, the conductors may be maintained separate from cooling fluids passing through the interface 604 from the cooling arrangement 501 to the X-ray tube 502.

The cooling arrangement 501 comprises a pump 620, an outlet passage 632, serpentine passage 622 a pump inlet passage 642 and a fan 624. The pump 620, outlet passage 632, serpentine passage 622 all being fluidly coupled to an interior volume 614 of an x-ray tube 502. The pump 620 may be one or more of a hydraulic, pneumatic, electric, and mechanical pump. In one example, the pump 620 is electric. The pump 620 may pressurize and direct a cooling fluid through a pump outlet passage 632 through the serpentine passage 622 which is fluidly connected to an intermediate tube to a first adapter 634 connected to an interface fluidly connecting an intermediate tube 640 to the interior volume 614 of the X-ray tube 502. In one example, the cooling fluid is dielectric oil, however, other cooling fluids may be used without departing from the scope of the present disclosure. As illustrated, the pump inlet passage 642 may be arranged between the fan 624 and the serpentine passage 622. A first adapter 634 may extend through the interface 604, wherein the first adapter 634 may fluidly couple the intermediate passage 640 to the interior volume 614 of the X-ray tube 502. The second adapter 638 may be shaped to sealingly engage with the pump inlet passage 642 so that all liquid in the interior volume 614 flows to the pump inlet passage 642.

As shown, the interior volume 614 receives liquid from a lower region, below the housing 610. As such, the liquid may flow up and at least partially fill the interior volume 614. A suction device may be arranged in an upper region of the interior volume 614. In one example, the suction device is adjacent to the first adapter 634. In some examples, the suction device may be arranged adjacent to the outer circumferential wall 506. The example of FIG. 6 merely illustrates one example of the X-ray tube 502 being positioned within the clearance 510. It will be appreciated that a greater portion or a smaller portion of the X-ray tube 502 may be arranged within the clearance 510 than that depicted in FIG. 6. The suction device may utilize vacuum, which may be generated via the pump 620 or via an auxiliary device, to draw liquid out of the interior volume 614 and to a first adapter 638 fluidly coupled to a pump inlet passage 642.

Liquid in the serpentine passage 622 may reverse in flow direction as it moves from the first tube to a second tube. In one example, the liquid in the serpentine passage reverses flow direction at it passes to a neighboring tube. The liquid may exit the serpentine passage 622 at a lower region near the inner circumferential wall 512 before flowing upward though an x-ray tube 502 interior volume 614 and into a pump inlet passage 642. The pump inlet passage 642 is fluidly coupled to the pump 620.

In one example, the individual tubes of the serpentine passage 622 may be parallel with one another, wherein U-shaped tubes may fluidly couple neighboring tubes. The U-shaped tubes may invert a coolant flow as coolant flows from one tube to another.

The fan 624 may be configured to rotate such that a breeze is generated. In one example, the breeze may cool liquid in the serpentine passage 622 and in the pump inlet passage 642. By arranging the pump inlet passage 642 between the serpentine passage 622 and the fan 624, a cooling effect experience by liquid in the pump inlet passage 642 may be increased relative to liquid in the serpentine passage 622, which may enhance cooling. In one example, a vent 644 is arranged within the housing 602 such that air within the cooling arrangement 501 may be released to atmosphere. The interface 604 may block gas transfer between the cooling arrangement 501 and the X-ray tube 502. That is to say, fluids outside of the pump outlet passage 632 and the suction device 636 may not flow between the cooling arrangement 501 and the X-ray tube 502.

The cooling arrangement 501 may be activated, which may include activating the pump 620 in response to a cooling demand from the X-ray tube 502. In one example, the X-ray tube 502 may comprise a temperature sensor configured to sense a temperature of a portion of the X-ray tube 502. In one example, the temperature sensor may sense a temperature of the cathode 611. Additionally or alternatively, the pump 620 may be activated in response to a threshold time elapsed following a start of a scanning procedure. In one example, the threshold time elapsed is a fixed value. Alternatively, the threshold time elapsed is a dynamic value, which may be adjusted based on scan type, current flow, previous scan duration, and time elapsed between a previous scan and a current scan. For example, the threshold time elapsed may decrease as the time elapsed between the previous scan and the current scan decreases.

In this way, an entirety of the cooling arrangement and the X-ray tube are arranged within the housing and adjacent to the first end of the C-arm of the X-ray system. As such, other portions of the C-arm, including the second end, are free of any components of the cooling arrangements. In one example, the cooling arrangement is limited to being located to only within a boundary of the housing and does not extend beyond the boundary of the housing. Additionally or alternatively, passages of the cooling arrangement are routed through only the cooling arrangement, the interface, and into the X-ray tube.

Thus, in one aspect, a mobile X-ray device may comprise a C-arm comprising an X-ray source arranged at a first end and a detector arranged at a second end, opposite the first end. A cooling arrangement may be arranged only at the first end within a housing of the X-ray source. The technical effect of arranging an entirety of the cooling arrangement adjacent to the X-ray source is to enhance cooling and decrease packaging size and weight.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control system, where the described actions are carried out by executing the instructions in a system including the various hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An X-ray system, comprising:
a base unit configured to support and transport the mobile X-ray system;
a moveable arm comprising an X-ray source arranged at a first end and an X-ray detector arranged at a second end, wherein the moveable arm comprises a clearance, wherein the clearance does not extend to the first end of the moveable arm; and
a fluid-circulating cooling arrangement having a pump arranged within a housing shared with the X-ray source at the first end of the moveable arm;
wherein the fluid-circulating cooling arrangement includes passages for circulating a fluid therethrough; and
wherein the pump circulates the fluid through the passages and into an interior volume of the X-ray source.

2. The X-ray system of claim 1, wherein the fluid-circulating cooling arrangement is directly adjacent to the X-ray source.

3. The X-ray system of claim 1, wherein the X-ray source is at least partially positioned within the clearance.

4. The X-ray system of claim 1, wherein the moveable arm is coupled to the base unit.

5. The X-ray system of claim 4, wherein the moveable arm moves independently of the base unit.

6. The X-ray system of claim 1, wherein the fluid-circulating cooling arrangement comprises a fan, a plurality of radiator coils, a pump outlet passage, and a pump inlet passage, and wherein each of the fan, the plurality of radiator coils, the pump outlet passage, and the pump inlet passage are arranged within the housing.

7. The X-ray system of claim 6, wherein the pump outlet passage is configured to flow the fluid from the pump through the radiator coils to the interior volume of the X-ray source.

8. The X-ray system of claim 6, wherein the pump inlet passage is arranged between the fan and the plurality of radiator coils.

9. The X-ray system of claim 1, wherein the fluid is dielectric oil.

10. The X-ray system of claim 1, wherein an interface is arranged directly between the fluid-circulating cooling arrangement and the X-ray source.

11. An X-ray device, comprising:
a cooling arrangement comprising a pump fluidly coupled to a pump outlet passage and a pump inlet passage, a fan, and a plurality of radiator coils, wherein the pump inlet passage is arranged between the plurality of radiator coils and the fan; and
an X-ray source arranged within a housing configured to house an entirety of the X-ray source and the cooling arrangement only at one end of a moveable C-arm, wherein an interface is arranged directly between the cooling arrangement and the X-ray source through which the pump circulates a liquid coolant into an interior volume of an X-ray tube of the X-ray source.

12. The X-ray device of claim 11, wherein the moveable C-arm comprises an interior space between at least three walls in which the X-ray source and the cooling arrangement are arranged, wherein the housing comprises an X-ray outlet, and wherein the housing encloses the X-ray source, except for air transfer through the cooling arrangement.

13. The X-ray device of claim 11, further comprising a second end opposite the first end, wherein an X-ray detector is arranged at the second end, wherein a portion of the C-arm between the housing and the second end is free of cooling arrangement components.

14. The X-ray device of claim 11, wherein the liquid coolant is dielectric oil.

15. The X-ray device of claim 11, wherein the X-ray device is a mobile X-ray device comprising a base unit with wheels, wherein the base unit is free of cooling arrangement components.

16. A mobile imaging system, comprising:
a base unit for moving within a room and from room to room;
a C-arm coupled to the base unit including an X-ray source at a first end and a detector at a second end opposite the first end, wherein the C-arm comprises an interior clearance separating an inner circumferential wall and an outer circumferential wall; and
an opening arranged in the inner circumferential wall, shaped to receive the X-ray source and a cooling arrangement, wherein the opening does not extend to the first end of the C-arm, wherein the cooling arrangement is fluidly coupled to an interior volume of the X-ray source via a pump inlet passage, wherein a housing is configured to house each of the X-ray source and the cooling arrangement; and
wherein the housing is arranged only at the first end, and wherein all components of the cooling arrangement and the X-ray source are contained within the housing.

17. The mobile imaging system of claim 16, wherein the housing extends through the opening and is pressed against interior surfaces of the outer circumferential wall.

18. The mobile imaging system of claim 16, wherein components of the cooling arrangement comprise a pump, a plurality of radiator coils, a fan, a pump outlet passage, a pump inlet passage, and an intermediate passage.

19. The mobile imaging system of claim 16, wherein the C-arm is configured to rotate isocentrically around a rotational axis arranged between the first end and the second end, and the base unit is configured to support the mobile imaging system and transport the mobile imaging system to different locations, wherein the C-arm and the base unit move independent of one another.

20. The mobile imaging system of claim 16, wherein an interface is arranged directly between the cooling arrangement and the X-ray source through which the pump circulates a liquid coolant into an interior volume of an X-ray tube of the X-ray source.

* * * * *